(12) United States Patent  (10) Patent No.: US 7,775,973 B2
Okada et al.  (45) Date of Patent: Aug. 17, 2010

(54) ENDOSCOPE SYSTEM

(75) Inventors: Tsutomu Okada, Tachikawa (JP); Jin Ito, Tokyo (JP)

(73) Assignee: Olympus Medical Systems Corp. (JP)

( * ) Notice: Subject to any disclaimer, the term of this patent is extended or adjusted under 35 U.S.C. 154(b) by 357 days.

(21) Appl. No.: 12/035,762

(22) Filed: Feb. 22, 2008

(65) Prior Publication Data

US 2008/0208004 A1    Aug. 28, 2008

Related U.S. Application Data

(63) Continuation of application No. PCT/JP2006/316332, filed on Aug. 21, 2006.

(30) Foreign Application Priority Data

Aug. 24, 2005 (JP) .............................. 2005-242938

(51) Int. Cl.
*A61B 1/12* (2006.01)

(52) U.S. Cl. ................. 600/156; 600/104; 600/153; 600/154; 600/158; 600/159; 600/562; 600/565; 600/571; 600/573; 606/113; 606/114; 606/115

(58) Field of Classification Search ................. 600/104, 600/153–154, 156, 158–159, 562, 564–566, 600/570–571, 573; 606/113–115
See application file for complete search history.

(56) References Cited

U.S. PATENT DOCUMENTS

| | | | | |
|---|---|---|---|---|
| 4,083,706 A | * | 4/1978 | Wiley | 55/385.1 |
| 4,794,913 A | * | 1/1989 | Shimonaka et al. | 600/159 |
| 4,968,309 A | * | 11/1990 | Andersson | 604/534 |
| 5,749,829 A | * | 5/1998 | Yokoi et al. | 600/153 |
| 5,971,917 A | * | 10/1999 | Komi et al. | 600/159 |
| 6,068,603 A | * | 5/2000 | Suzuki | 600/565 |

(Continued)

FOREIGN PATENT DOCUMENTS

DE    199 06 592    2/1999

(Continued)

OTHER PUBLICATIONS

International Search Report dated Nov. 7, 2006 issued in corresponding PCT Application No. PCT/JP2006/316332.

(Continued)

*Primary Examiner*—Matthew J Kasztejna
(74) *Attorney, Agent, or Firm*—Ostrolenk Faber LLP

(57) ABSTRACT

An endoscope of an endoscope system includes a channel of which a distal end forms a distal opening at a distal end of an insertion portion, of which a proximal end forms a proximal opening at an operating portion, and used for at least suction, and a suction duct of which a distal end forms a suction opening at the operating portion and of which a proximal end is connected to a suction device. An endoscopic accessory includes a capture portion to be connected to an accessory insertion portion and detachably attached to the operating portion of the endoscope, and the capture portion includes a communication path to communicate the proximal opening with the suction opening when the capture portion is attached to the endoscope, and a capture unit interposed in the communication path and to capture the tissue being sucked from the channel into the suction duct.

8 Claims, 18 Drawing Sheets

U.S. PATENT DOCUMENTS

| | | | |
|---|---|---|---|
| 6,110,127 A * | 8/2000 | Suzuki | 600/565 |
| 6,142,956 A * | 11/2000 | Kortenbach et al. | 600/564 |
| 6,632,182 B1 * | 10/2003 | Treat | 600/564 |
| 2004/0220452 A1 * | 11/2004 | Shalman | 600/157 |
| 2005/0027165 A1 * | 2/2005 | Rovegno | 600/154 |
| 2005/0119522 A1 * | 6/2005 | Okada | 600/106 |

FOREIGN PATENT DOCUMENTS

| | | |
|---|---|---|
| JP | 62-74804 | 5/1987 |
| JP | 01-160525 | 6/1989 |
| JP | 06-014991 | 1/1994 |
| JP | 07-059729 | 3/1995 |
| JP | 11-226024 | 8/1999 |
| JP | 11-267089 | 10/1999 |
| JP | 2000-237126 | 9/2000 |
| JP | 2005-152502 | 6/2005 |
| JP | 2005-211453 | 8/2005 |
| WO | WO 2004/075740 | 9/2004 |

OTHER PUBLICATIONS

Written Opinion dated Nov. 7, 2006 issued in corresponding PCT Application No. PCT/JP2006/316332.

Letter from German associate dated Jun. 5, 2009 forwarding the Search Report dated May 8, 2009 to Japanese associate, including discussion of relevancy thereof.

Search Report issued by European Patent Office in connection with corresponding application No. EP 06 79 6595 on May 8, 2009.

* cited by examiner

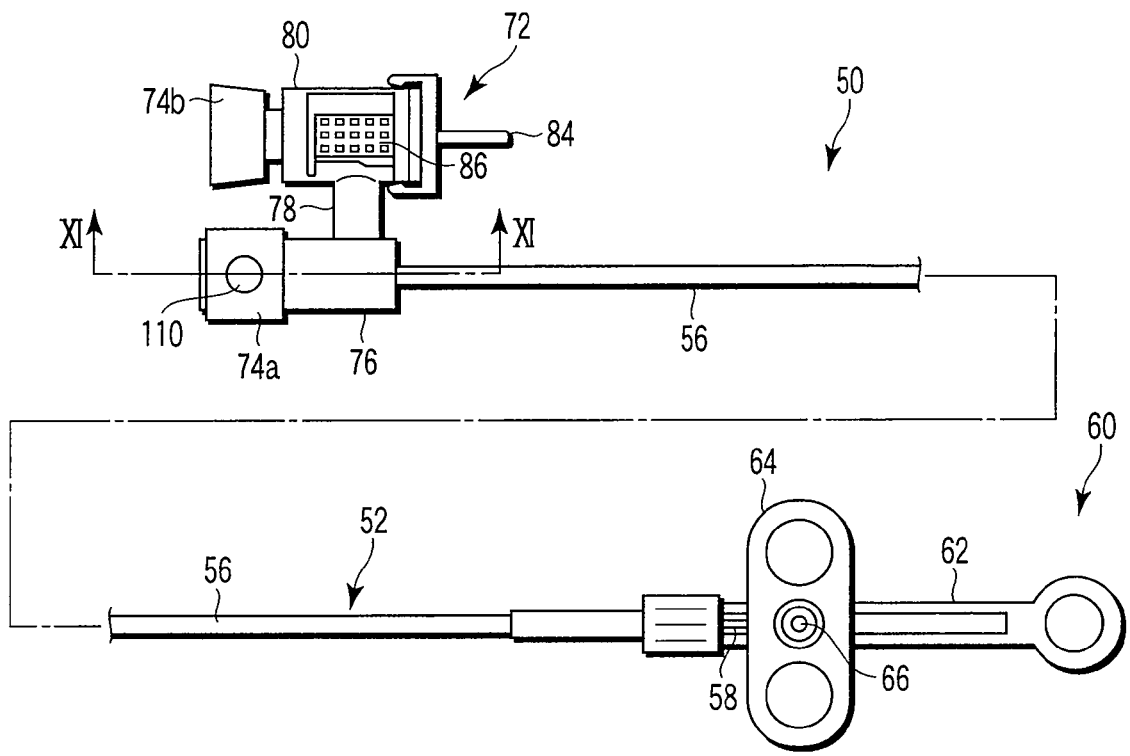
F I G. 10
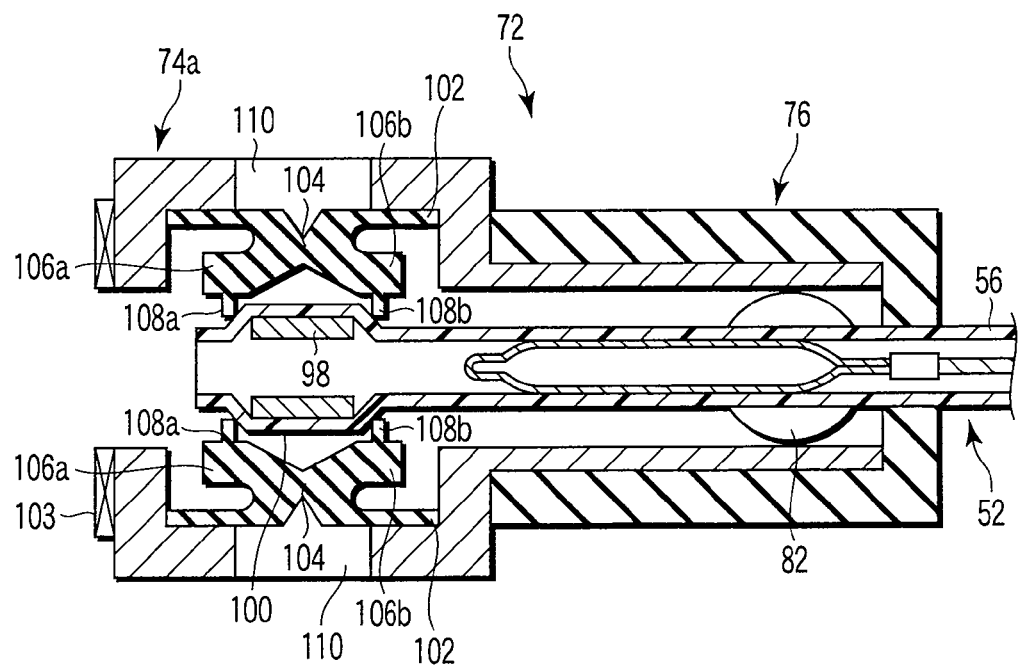
F I G. 11

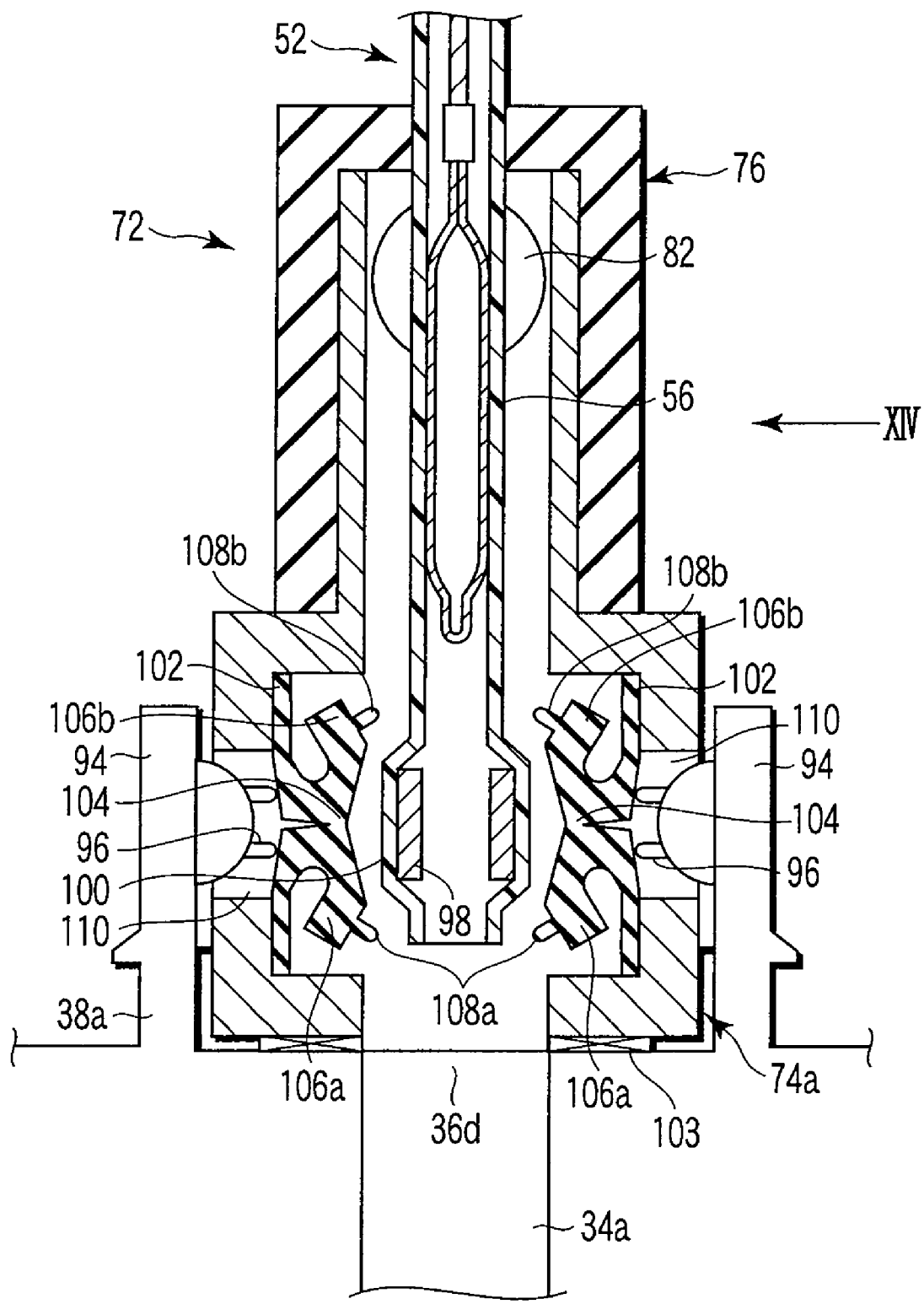
F I G. 13

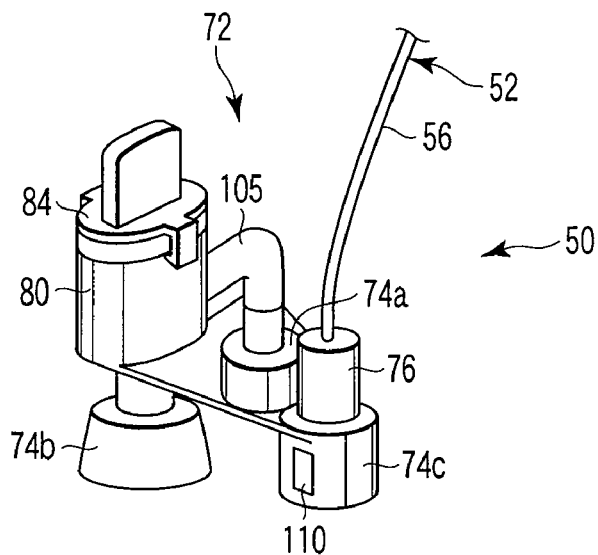
F I G. 17
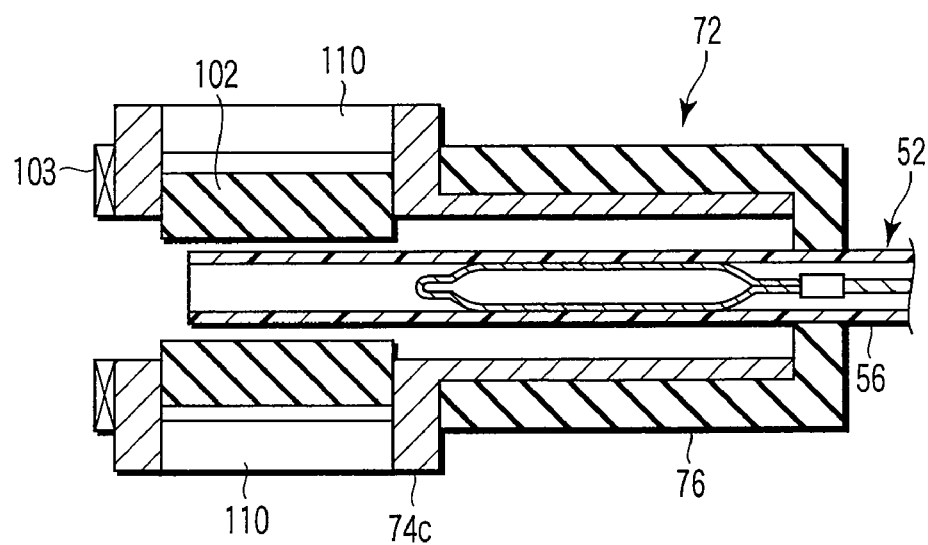
F I G. 18A

ENDOSCOPE SYSTEM

CROSS-REFERENCE TO RELATED APPLICATIONS

This is a Continuation Application of PCT Application No. PCT/JP2006/316332, filed Aug. 21, 2006, which was published under PCT Article 21(2) in Japanese.

This application is based upon and claims the benefit of priority from the prior Japanese Patent Application No. 2005-242938, filed Aug. 24, 2005, the entire contents of which are incorporated herein by reference.

BACKGROUND OF THE INVENTION

1. Field of the Invention

The present invention relates to an endoscope system to separate a part of a living tissue therefrom in a body cavity under observation with an endoscope and gather the separated tissue by suction.

2. Description of the Related Art

Heretofore, an endoscope system has been used, the endoscope system to separate a part of a living tissue therefrom in a body cavity under observation with an endoscope by use of an endoscopic accessory and gather the separated tissue by suction so that the gathered tissue is used in a pathological examination.

As the endoscopic accessory in such an endoscope system, for example, a high-frequency snare is used. In the high-frequency snare, a polyp, a mucosal tissue or the like is tightened with a loop at a distal end of the snare, and a high-frequency current is passed through the loop to cut the polyp, the mucosal tissue or the like.

Moreover, to suck and gather the tissue, the following device is used. For example, an endoscope and a suction bottle are used to suck and gather the tissue. That is, in the endoscope, an operating portion is provided at a proximal end of an insertion portion insertable into the body cavity, and this operating portion is connected to a controller for controlling the endoscope via a connecting portion. A suction passage passes from a distal end of the insertion portion through the insertion portion, the operating portion and the connecting portion to communicate with the suction bottle, and the tissue is sucked and gathered into the suction bottle via the suction passage. In U.S. Pat. No. 5,624,418, a gather device is disclosed, the gather device to be arranged in front of such a suction bottle and separate and capture the tissue from blood, soil and the like being sucked together with the tissue. In Jpn. Utility Model Appln. KOKAI Publication No. 62-74804, a mesh basket is disclosed, the mesh basket to be detachably interposed in a suction passage at an operating portion of an endoscope and separate and capture the tissue from the blood, the soil and the like. In such an endoscope, a path through which the tissue is sucked is short, and hence the tissue is scarcely damaged during the suction.

Furthermore, in paragraphs "0099" to "0117" of Detailed Description of the Invention in Jpn. Pat. Appln. KOKAI Publication No. 11-226024, an endoscope system is disclosed to suck and gather a tissue using an endoscopic accessory and a specimen trap. That is, in the endoscopic accessory, a suction lumen is formed in a sheath insertable into the body cavity, and the specimen trap is connected to a proximal end of the suction lumen. Thus, the tissue is sucked into the specimen trap via the suction lumen, and then separated and captured from blood, soil and the like by a specimen filter disposed in the specimen trap.

BRIEF SUMMARY OF THE INVENTION

In an aspect of the present invention, an endoscope system includes: an endoscope; and an endoscopic accessory, the endoscope including: an elongated insertion portion insertable from a distal end thereof into a body cavity; an operating portion connected to a proximal end of the insertion portion; a channel provided at the insertion portion and the operating portion, of which a distal end forms a distal opening at the distal end of the insertion portion, of which a proximal end forms a proximal opening at the operating portion, and used for at least suction; and a suction duct provided at the operating portion, of which a distal end forms a suction opening at the operating portion, and of which a proximal end is connected to a suction device, and the endoscopic accessory including: an elongated accessory insertion portion insertable from a distal end thereof into the body cavity; a treatment portion provided at the distal end of the accessory insertion portion and to separate a part of a living tissue therefrom; and a capture portion to be connected to the accessory insertion portion and detachably attached to the operating portion of the endoscope, and the capture portion including: a communication path to communicate the proximal opening with the suction opening when the capture portion is attached to the endoscope; and a capture unit interposed in the communication path and to capture the tissue being sucked from the channel into the suction duct.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 10 is a side view showing a high-frequency snare of the endoscope system according to the second embodiment of the present invention;

FIG. 11 is a longitudinal cross sectional view along the XI-XI line of FIG. 10, showing a first connection member and its periphery of the high-frequency snare according to the second embodiment of the present invention;

FIG. 13 is a longitudinal cross sectional view showing a state wherein the first connecting portion of the high-frequency snare is attached to the insertion connecter of the endoscope in the endoscope system according to the second embodiment of the present invention;

FIG. 17 is a perspective view showing a trap portion and its periphery of the high-frequency snare of the endoscope system according to the third embodiment of the present invention;

FIG. 18A is a longitudinal cross sectional view along the XVIIIA-XVIIIA line of FIG. 16A, showing a third connection member and its periphery of the high-frequency snare of the endoscope system according to the third embodiment of the present invention;

DETAILED DESCRIPTION OF THE INVENTION

Figure 1:
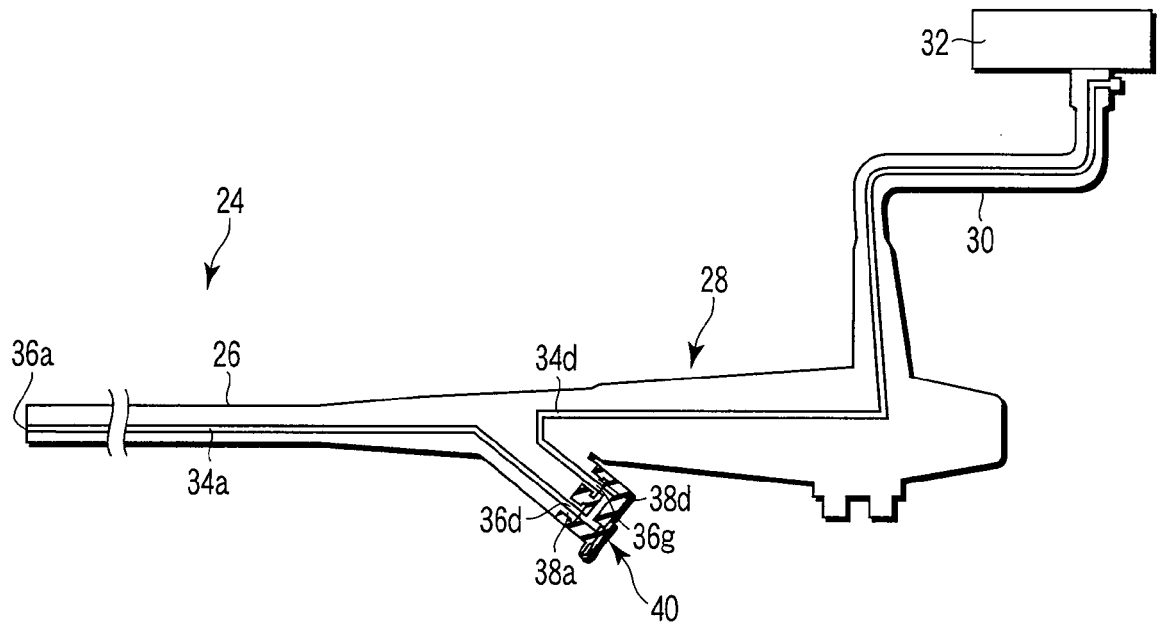
FIG. 1 is a schematic diagram showing an endoscope of an endoscope system according to a first embodiment of the present invention.
Figure 2:
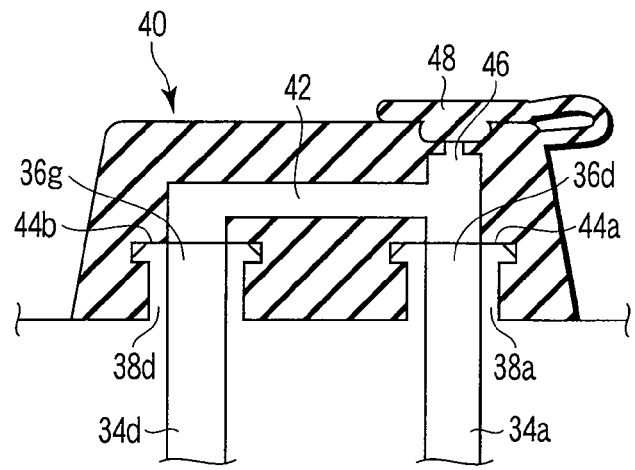
FIG. 2 is a cross sectional view showing a connector and a plug member of the endoscope of the endoscope system according to the first embodiment of the present invention.

A first embodiment of the present invention will hereinafter be described with reference to FIGS. 1 to 8. FIGS. 1 and 2 show an endoscope 24 of an endoscope system according to the present embodiment. As shown in FIG. 1, this endoscope 24 includes an elongated insertion portion 26 insertable into a body cavity. A proximal end of this insertion portion 26 is provided with an operating portion 28 to be held and operated by an operator. A connecting portion 30 is extended from this operating portion 28, and an extended end of this connecting portion 30 is connected to a control unit 32 for controlling the endoscope 24. It is to be noted that the control unit 32 is provided with a light source for supplying illumination light to the endoscope 24 and the like.

A channel 34a for insertion of various accessories and suction is formed over the insertion portion 26 and the operating portion 28. A distal end of this channel 34a forms a distal opening 36a at a distal end of the insertion portion 26, and a proximal end of the channel 34a forms an insertion port 36d as a proximal opening at an insertion connecter 38a of the operating portion 28. A suction duct 34d for the suction is formed over the operating portion 28 and the connecting portion 30. A distal end of this suction duct 34d forms a suction opening 36g in a suction connecter 38d provided in the vicinity of the insertion connecter 38a. A proximal end of the suction duct 34d extends to the extended end of the connecting portion 30, and is connected to a suction device such as a suction bottle.

As shown in FIG. 2, a plug member 40 formed of an elastic material such as a rubber is detachably attached to the insertion connecter 38a and the suction connecter 38d. One end of a communication path 42 formed at this plug member 40 is provided with a first engagement portion 44a to be engaged with the insertion connecter 38a airtightly to communicate the insertion port 36d with the communication path 42. The other end of the communication path 42 is provided with a second engagement portion 44b to be engaged with the suction connecter 38d airtightly to communicate the suction opening 36g with the communication path 42. A branch path is extended from the communication path 42 so as to lengthen the channel 34a in a state wherein the plug member 40 is attached to the insertion connecter 38a, and the branch path opens at an outer surface of the plug member 40 to form a channel opening 46 into which various accessories is insertable. The plug member 40 is provided with a lid member 48 to detachably cover the channel opening 46 to close the channel opening 46 airtightly.

Referring to FIGS. 1 and 2, in a state wherein the plug member 40 is attached to the endoscope 24 and the lid member 48 is attached to the channel opening 46, the channel 34*a* communicates with the suction duct 34*d* via the communication path 42 to allow the suction from the distal opening 36*a* of the distal end of the insertion portion 26, through the channel 34*a*, the communication path 42 and the suction duct 34*d*. Moreover, in a state wherein the lid member 48 is detached from the channel opening 46, various accessories is insertable into the insertion port 36*d* from the channel opening 46, through the channel 34*a* and protruded from the distal opening 36*a*. In this manner, through the attachment of the plug member 40 to the endoscope 24, the endoscope 24 can be used alone.

Figure 3:
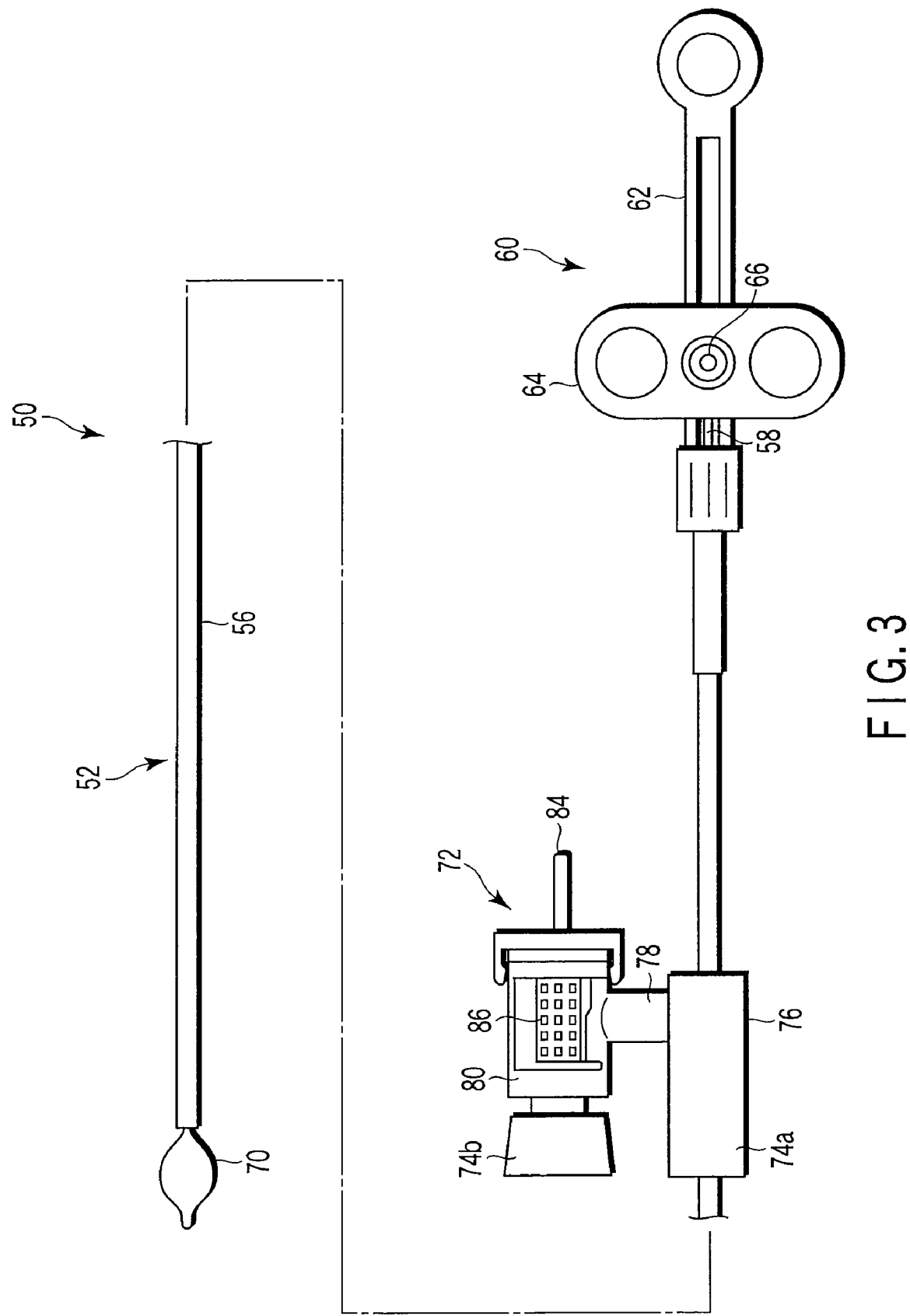
FIG. 3 is a side view showing a high-frequency snare of the endoscope system according to the first embodiment of the present invention.
Figure 4:
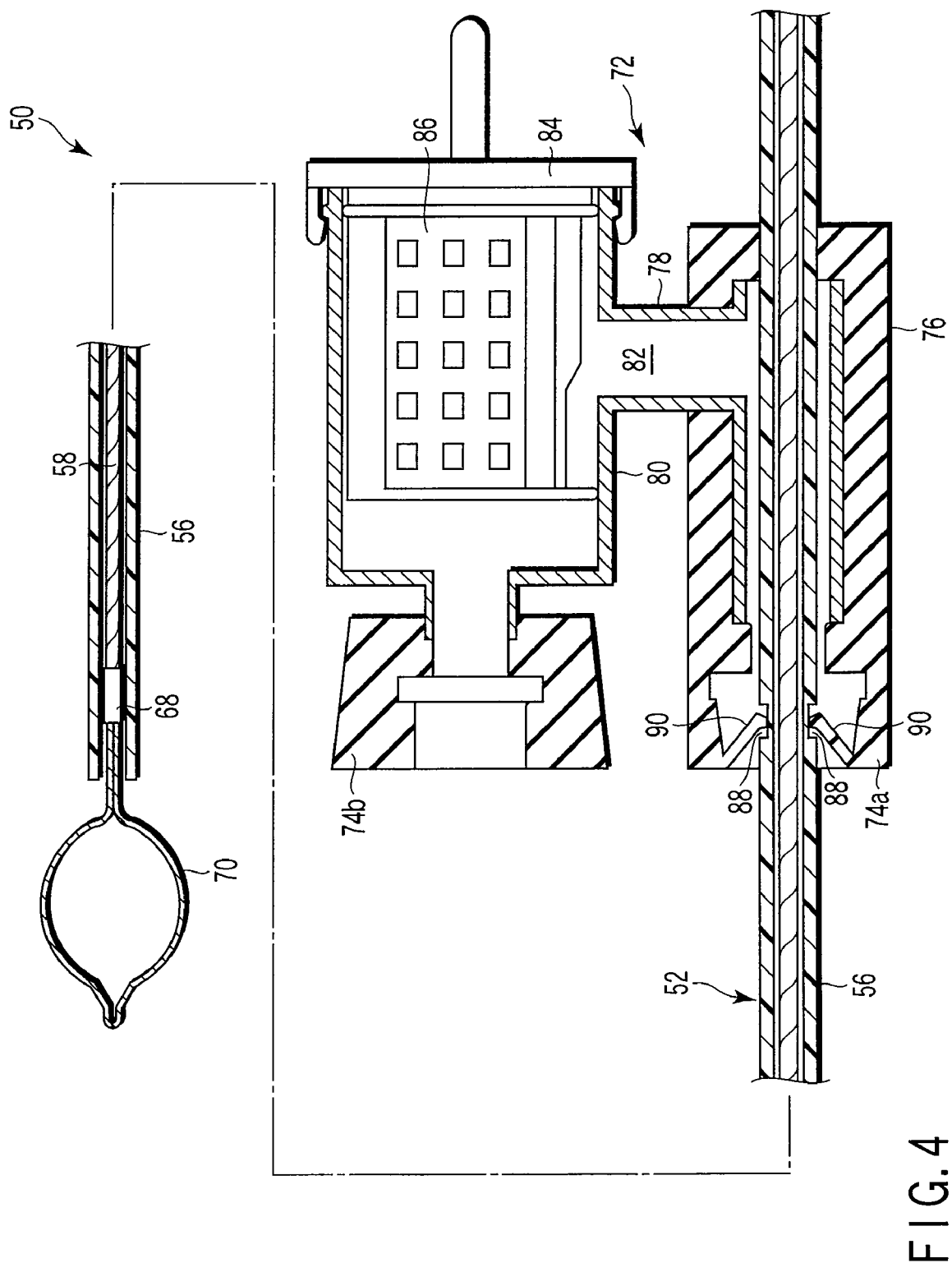
FIG. 4 is a longitudinal cross sectional view showing the high-frequency snare of the endoscope system according to the first embodiment of the present invention.

FIGS. 3 and 4 show a high-frequency snare 50 as the endoscopic accessory of the endoscope system according to the present embodiment. This high-frequency snare 50 includes a snare portion 52 for cutting a polyp or the like in a body cavity. This snare portion 52 includes a sheath 56 as an accessory insertion portion insertable into the body cavity. An operation wire 58 is inserted through this sheath 56, and a proximal end of this operation wire 58 is connected to a slider 64 of a snare operating portion 60 provided at a proximal end of the sheath 56. The operation wire 58 is movable forward and backward through forward and backward movement of the slider 64 with respect to a main body portion 62 of the snare operating portion 60. It is to be noted that the proximal end of the operation wire 58 is connected to an electrode 66 in the slider 64, and through connecting a high-frequency power source to this electrode 66, a high-frequency current can be passed through the operation wire 58.

On the other hand, a distal end of the operation wire 58 is connected to a cutting wire 70 as a treatment portion via a connection chip 68. The high-frequency current is to be passed through this cutting wire 70 via the operation wire 58 and the connection chip 68. The cutting wire 70 is beforehand kinked so that the cutting wire 70 is elastically deformed to be crushed into an elongated shape when the operation wire 58 is moved backward and drawn into the sheath 56 and the cutting wire 70 is expanded and opened into a loop shape when the operation wire 58 is moved forward and protruded from the sheath 56.

Referring to FIGS. 1 to 4, a trap portion 72 as a capture portion is connected to the snare portion 52 of the high-frequency snare 50, the trap portion 72 to be attached to the endoscope 24, and separate and capture the polyp or the like being sucked from the channel 34*a* to the suction duct 34*d*, from blood, soil and the like.

In the trap portion 72, inner cavities of a first connection member 74*a*, an insertion tube 76, a side tube 78, a case 80 and a second connection member 74*b* form a communication path 82 to communicate the channel 34*a* with the suction duct 34*d* when the trap portion 72 is attached to the endoscope 24. That is, the trap portion 72 is provided with the first connection member 74*a* formed of an elastic material and to be connected to the insertion connecter 38*a* of the endoscope 24 airtightly to communicate the insertion port 36*d* with the communication path 82. This first connection member 74*a* is integrally connected to one end of the insertion tube 76 formed of an elastic material. This insertion tube 76 is connected to the case 80 via the side tube 78 extending in a radial direction of the insertion tube 76. This case 80 is formed of a transparent material and the inside of the case can be observed. Moreover, a trap 84 is detachably attached to the case 80, and this trap 84 is provided with a mesh portion 86 as a capture unit to be interposed in the communication path 82, and separate and capture the polyp or the like being sucked along the communication path 82, from the blood, the soil and the like. Then, the second connection member 74*b* is connected to the case 80, the second connection member 74*b* formed of an elastic material and to be connected to the suction connecter 38*d* of the endoscope 24 airtightly to communicate the communication path 82 with the suction opening 36*g*.

Moreover, the sheath 56 of the snare portion 52 is connected to the trap portion 72 so that the sheath 56 is movable forward and backward in a longitudinal axial direction thereof. That is, the sheath 56 is extractably inserted through inner cavities of the insertion tube 76 and the first connection member 74*a* and movable forward and backward in the longitudinal axial direction thereof. It is to be noted that at the end of the insertion tube 76 opposite to the first connection member 74*a*, an end opening is closed through elastic deformation when the sheath 56 is extracted, to keep the communication path 82 airtight.

Furthermore, the sheath 56 of the snare portion 52 is fixed to the trap portion 72 when the trap portion 72 is detached from the endoscope 24 and this fixing is released when the trap portion 72 is attached to the endoscope 24. That is, an engagement groove 88 is formed at an outer peripheral surface of the sheath 56 of the snare portion 52, and an engagement member 90 to engage with the engagement groove 88 of the sheath 56 so as to engage the sheath 56 with the first connection member 74*a* is protruded from an inner peripheral surface of the first connection member 74*a* of the trap portion 72. It is to be noted that the arrangement of the engagement groove 88 with respect to the longitudinal axial direction of the sheath 56 is set so that the distal end of the sheath 56 does not protrude from the endoscope 24 in a state wherein the sheath 56 is inserted into the channel 34*a* of the endoscope 24 and the trap portion 72 is attached to the endoscope 24. On the other hand, when the trap portion 72 is attached to the endoscope 24 and the first connection member 74*a* is connected to the insertion connecter 38*a*, the engagement member 90 is pushed away by the insertion connecter 38*a*, and engagement between the engagement member 90 and the engagement groove 88 is released.

Thus, the insertion connecter 38*a*, the engagement groove 88 and the engagement member 90 form a switch mechanism to keep the high-frequency snare 50 in a fixed state wherein the sheath 56 is fixed to the trap portion 72 while the trap portion 72 is detached from the endoscope 24 and switch the high-frequency snare 50 to a released state wherein this fixing is released when the trap portion 72 is attached to the endoscope 24.

Next, an operation of the endoscope system according to the present embodiment will be described with reference to FIGS. 5 to 8. There will hereinafter be described a case wherein a polyp 92 is cut in a body cavity under observation with the endoscope and the cut polyp 92 is sucked and gathered.

Figure 5:
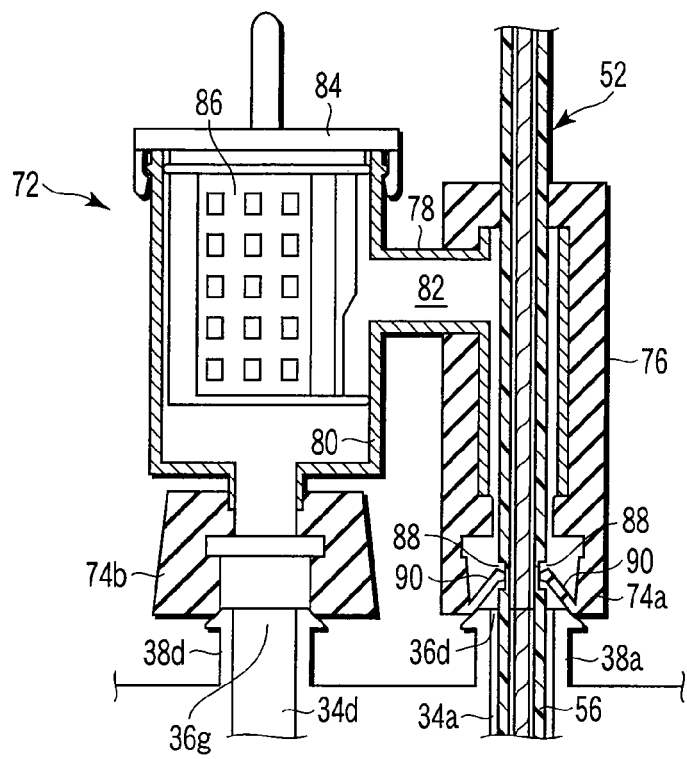
FIG. 5 is a longitudinal cross sectional view showing a state before a trap portion of the high-frequency snare is attached to the connecter of the endoscope in the endoscope system according to the first embodiment of the present invention.
Figure 6:
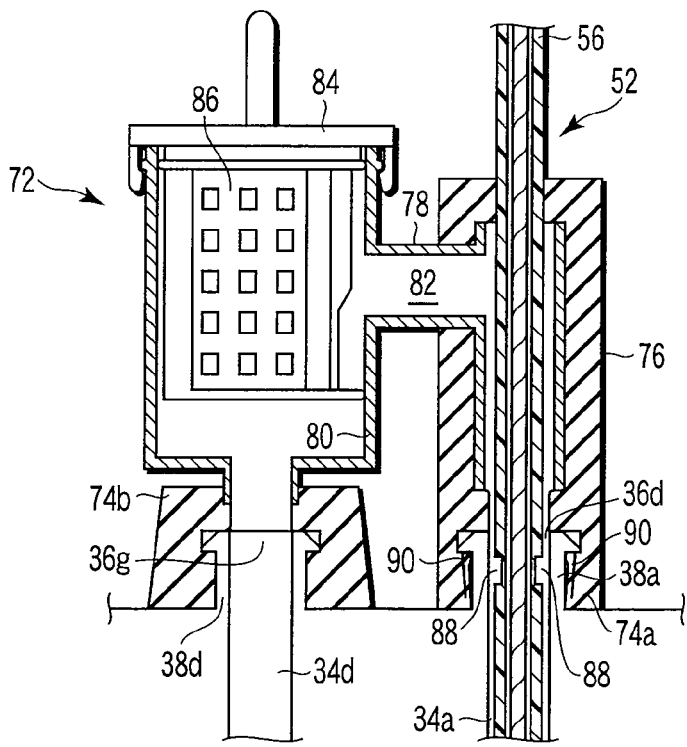
FIG. 6 is a longitudinal cross sectional view showing a state wherein the trap portion of the high-frequency snare is attached to the connecter of the endoscope in the endoscope system according to the first embodiment of the present invention.

First, the insertion portion 26 of the endoscope 24 is inserted into the body cavity, and the distal end of the insertion portion 26 is guided so that the polyp 92 falls into a view field. Then, as shown in FIG. 5, the plug member 40 is detached from the endoscope 24, and the sheath 56 of the high-frequency snare 50 is inserted into the insertion port 36*d* of the endoscope 24 and through the channel 34*a*. Subsequently, as shown in FIG. 6, the first connection member 74*a* of the trap portion 72 of the high-frequency snare 50 is connected to the insertion connecter 38*a* of the endoscope 24, and the second connection member 74*b* is connected to the suction connecter 38*d*, whereby the trap portion 72 is attached to the endoscope 24. In this case, the engagement member 90 is pushed away by the insertion connecter 38a to release the engagement between the engagement member 90 and the engagement groove 88, so that the sheath 56 become movable forward and backward with respect to the trap portion 72.

Subsequently, the sheath 56 is pushed inward to protrude the distal end of the sheath 56 from the distal opening 36a of the insertion portion 26 of the endoscope 24. Then, the slider 64 is moved forward with respect to the main body portion 62 of the snare operating portion 60, the cutting wire 70 is protruded from the distal end of the sheath 56 and expanded and opened into the loop shape, and the polyp 92 is caught by the cutting wire 70. Subsequently, the slider 64 is moved backward with respect to the main body portion 62, the cutting wire 70 is drawn into the sheath 56 and contracted and closed to tighten the polyp 92. In this state, the high-frequency power source is operated to pass the high-frequency current through the cutting wire 70, thereby cutting the polyp 92. Such an operation is repeated to cut a plurality of polyps 92.

Figure 7:
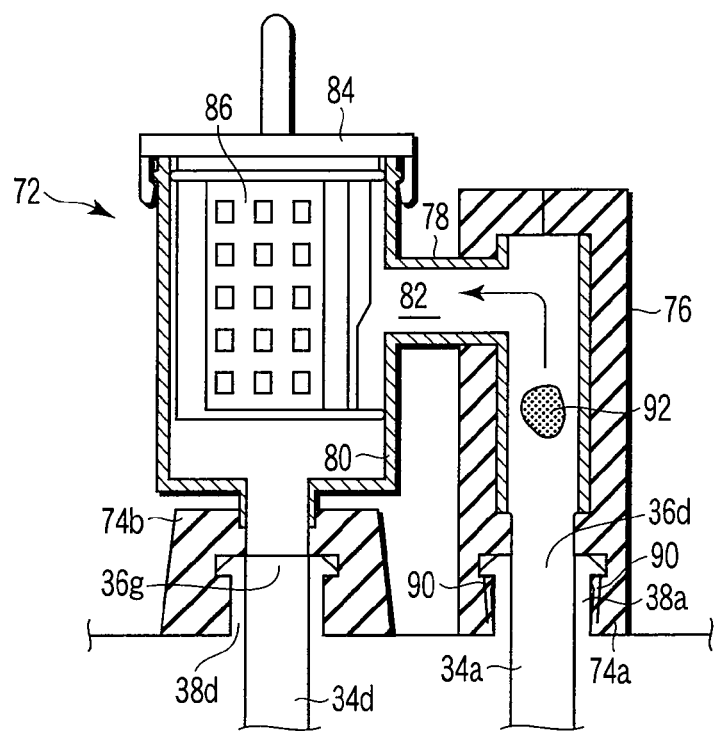
FIG. 7 is a longitudinal cross sectional view showing a capture of a polyp at the trap portion of the high-frequency snare in the endoscope system according to the first embodiment of the present invention.
Figure 8:
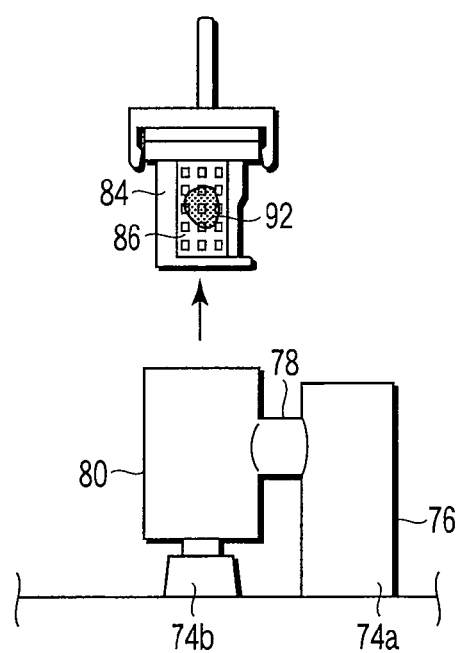
FIG. 8 is a diagram showing a state wherein a trap is detached from the trap portion of the high-frequency snare in the endoscope system according to the first embodiment of the present invention.

Afterward, the sheath 56 is pulled, and extracted from the channel 34a of the endoscope 24 and then from the insertion tube 76 of the capture portion 72. In this state, the suction device is operated to suck the cut polyp 92 from the distal opening 36a of the insertion portion 26 of the endoscope 24. As shown in FIG. 7, the sucked polyp 92 is sucked from the channel 34a of the endoscope 24 into the insertion tube 76, the side tube 78 and the case 80 of the trap portion 72, and separated from the blood, the soil and the like and captured, by the mesh portion 86 of the trap 84 in the case 80. Afterward, as shown in FIG. 8, the trap 84 is detached from the case 80, and the polyp 92 captured by the mesh portion 86 is gathered and sent for pathological examination.

Therefore, the endoscope system of the present embodiment produces the following effect. In the high-frequency snare 50 of the endoscope system according to the present embodiment, the snare portion 52 for cutting the polyp 92 in the body cavity is integrally connected to the trap portion 72 attached to the endoscope 24 and to capture the polyp 92 being sucked from the channel 34a into the suction duct 34d. Therefore, loss of the trap portion 72, which is comparatively small and easily lost, is prevented. Moreover, to prepare the endoscope system, through preparation of the high-frequency snare 50, both the snare portion 52 and the trap portion 72 is simultaneously prepared and do not have to be prepared separately or independently. Therefore, the preparation of the endoscope system is facilitated. Furthermore, to suck the polyp 92, the channel 34a of the endoscope 24 is used. Therefore, a cross sectional area of the suction passage orthogonal to the longitudinal axial direction thereof can be comparatively enlarged, and a suction and gather efficiency is increased.

Moreover, the sheath 56 of the high-frequency snare 50 is movable forward and backward in the longitudinal axial direction thereof with respect to the trap portion 72. Therefore, even when the trap portion 72 is attached to the endoscope 24, the distal end of the sheath 56 is movable forward and backward in the body cavity through operating the sheath 56 to move forward and backward with respect to the trap portion 72. Therefore, operability of the high-frequency snare 50 is improved.

Then, in the high-frequency snare 50, the sheath 56 is configured to be fixed to the trap portion 72 through engaging the engagement member 90 of the first connection member 74a of the trap portion 72 with the engagement groove 88 of the sheath 56 of the snare portion 52. Therefore, when the snare portion 52 is not used, the sheath 56 is fixed to the trap portion 72 so that an unnecessary movement of the sheath 56 is prevented. Especially, the sheath 56 is fixed to the trap portion 72 before attaching the trap portion 72 to the endoscope 24, whereby the sheath 56 is prevented from being improperly moved while the trap portion 72 is being attached to the endoscope 24.

Furthermore, when the trap portion 72 is attached to the endoscope 24, the engagement member 90 is pushed away by the insertion connecter 38a of the endoscope 24 to release the engagement between the engagement member 90 and the engagement groove 88, and the sheath 56 become automatically movable forward and backward with respect to the trap portion 72. In consequence, an operation for releasing the engagement between the engagement member 90 and the engagement groove 88 is not separately required, and operability of the high-frequency snare 50 is improved.

FIGS. 9A to 14 show a second embodiment of the present invention. A configuration having a function similar to that of the first embodiment is denoted with the same reference numerals, and description thereof is omitted. In the present embodiment, when the sheath of the snare portion is pushed forward with respect to the trap portion, the distal end of the sheath is inserted directly into the insertion port of the endoscope.

Figure 9A:
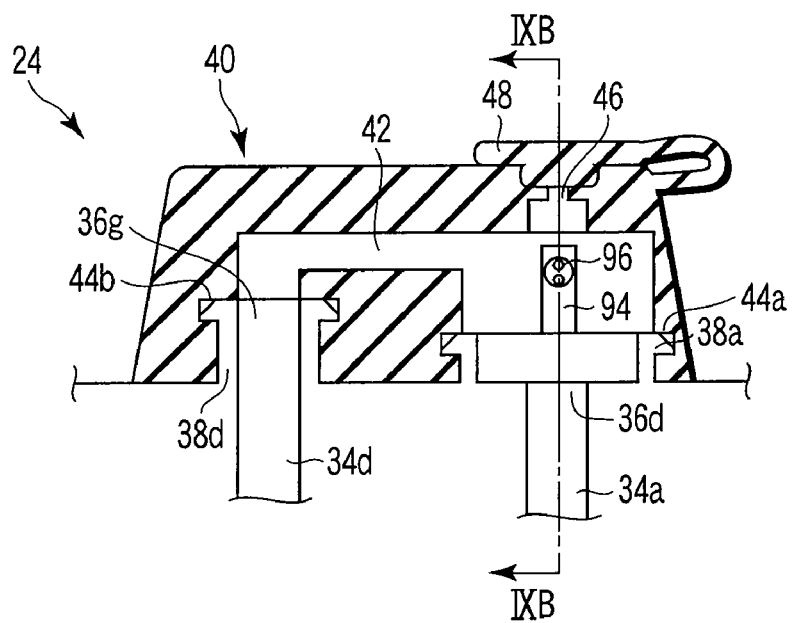
FIG. 9A is a cross sectional view showing a connecter and a plug member of an endoscope of an endoscope system according to a second embodiment of the present invention.
Figure 9B:
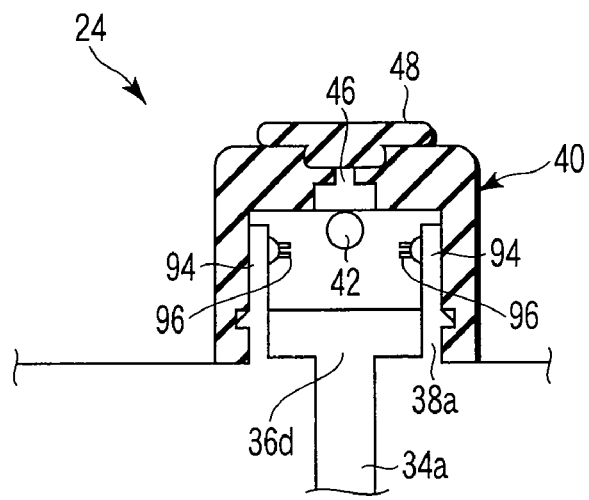
FIG. 9B is a cross sectional view along the IXB-IXB line of FIG. 9A, showing the connecter and the plug member of the endoscope of the endoscope system according to the second embodiment of the present invention.

FIGS. 9A and 9B show the insertion connecter 38a and the suction connecter 38d of the endoscope 24 of the endoscope system according to the present embodiment. A protruding end surface of the insertion connecter 38a of the endoscope 24 is provided with a pair of claw portions 94 protruded so as to face each other, and press protrusions 96 to cooperate with holding members 102 (see FIG. 11), described later, are formed on inner sides of the pair of claw portions 94, respectively.

FIGS. 10 and 11 show the high-frequency snare 50 of the endoscope system according to the present embodiment. A tubular member 98 fits into the distal end of the sheath 56 of the snare portion 52 of the high-frequency snare 50, and a protruding portion 100 is formed over the whole periphery of an outer peripheral surface of the distal end of the sheath 56.

Then, an inner peripheral surface of the first connection member 74a of the trap portion 72 is provided with a pair of holding members 102 so as to face each other, and the distal end of the sheath 56 is releasably held by the pair of holding members 102.

That is, in each holding member 102, a pair of arm portions 106a, 106b are extended from a hinge portion 104, and distal ends of the pair of arm portions 106a, 106b are provided with engagement protrusions 108a, 108b, respectively. The holding member 102 is formed of an elastic material, the pair of arm portions 106a, 106b are urged about the hinge portion 104 in a closing direction, and the engagement protrusions 108a, 108b of the pair of arm portions 106a, 106b are engaged with a distal end side and a rear end side of the protruding portion 100 at the distal end of the sheath 56, respectively. Thus, the distal end of the sheath 56 is held by the pair of holding members 102.

On the other hand, referring to FIGS. 9A to 11, window portions 110 are formed through the first connection member 74a on rear surface sides of the hinge portions 104 of the holding members 102. Then, when the trap portion 72 is attached to the endoscope 24 and the insertion connecter 38a of the endoscope 24 is connected to the first connection member 74a, the claw portions 94 of the insertion connecter 38a are arranged on an outer peripheral surface side of the first connection member 74a, and the press protrusions 96 of the claw portions 94 press back surfaces of the hinge portions 104 of the holding members 102 via the window portions 110. Then, the pressed holding members 102 are elastically deformed to open the pair of arm portions 106a, 106b about the hinge portion 104, engagement between the engagement protrusions 108a, 108b and the protruding portion 100 of the sheath 56 is released, and the sheath 56 become movable forward and backward with respect to the first connection member 74a.

In this manner, according to the present embodiment, the claw portions 94, the window portions 110 and the holding members 102 form the switch mechanism.

It is to be noted that the first connection member 74a is formed of a rigid material, and a connection end surface of the first connection member 74a is covered with a packing 103 for communicating the insertion port 36d of the endoscope 24 with the communication path 82 of the trap portion 72 airtightly.

Figure 12:
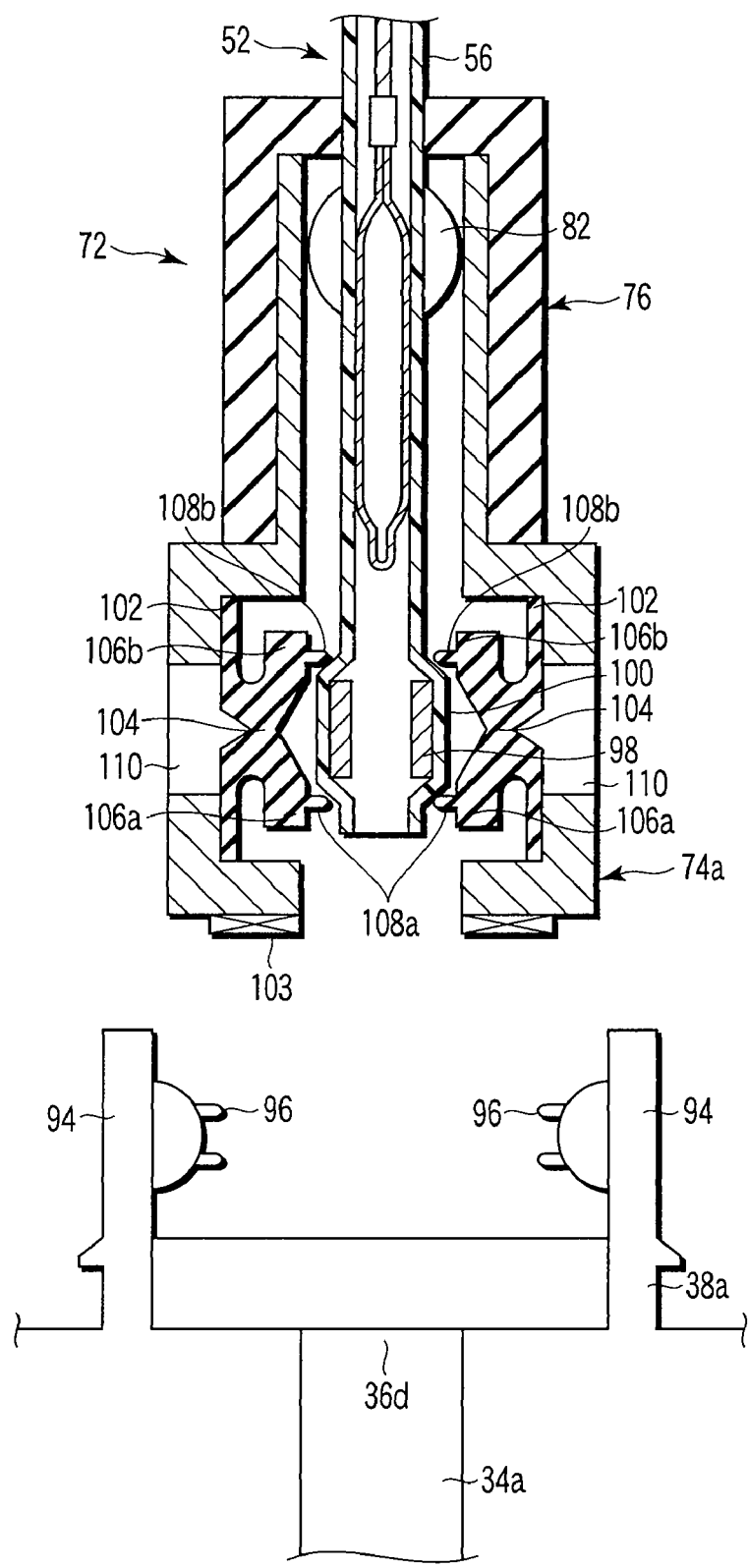
FIG. 12 is a longitudinal cross sectional view showing a state wherein the first connecting portion of the high-frequency snare is detached from the insertion connecter of the endoscope in the endoscope system according to the second embodiment of the present invention.
Figure 14:
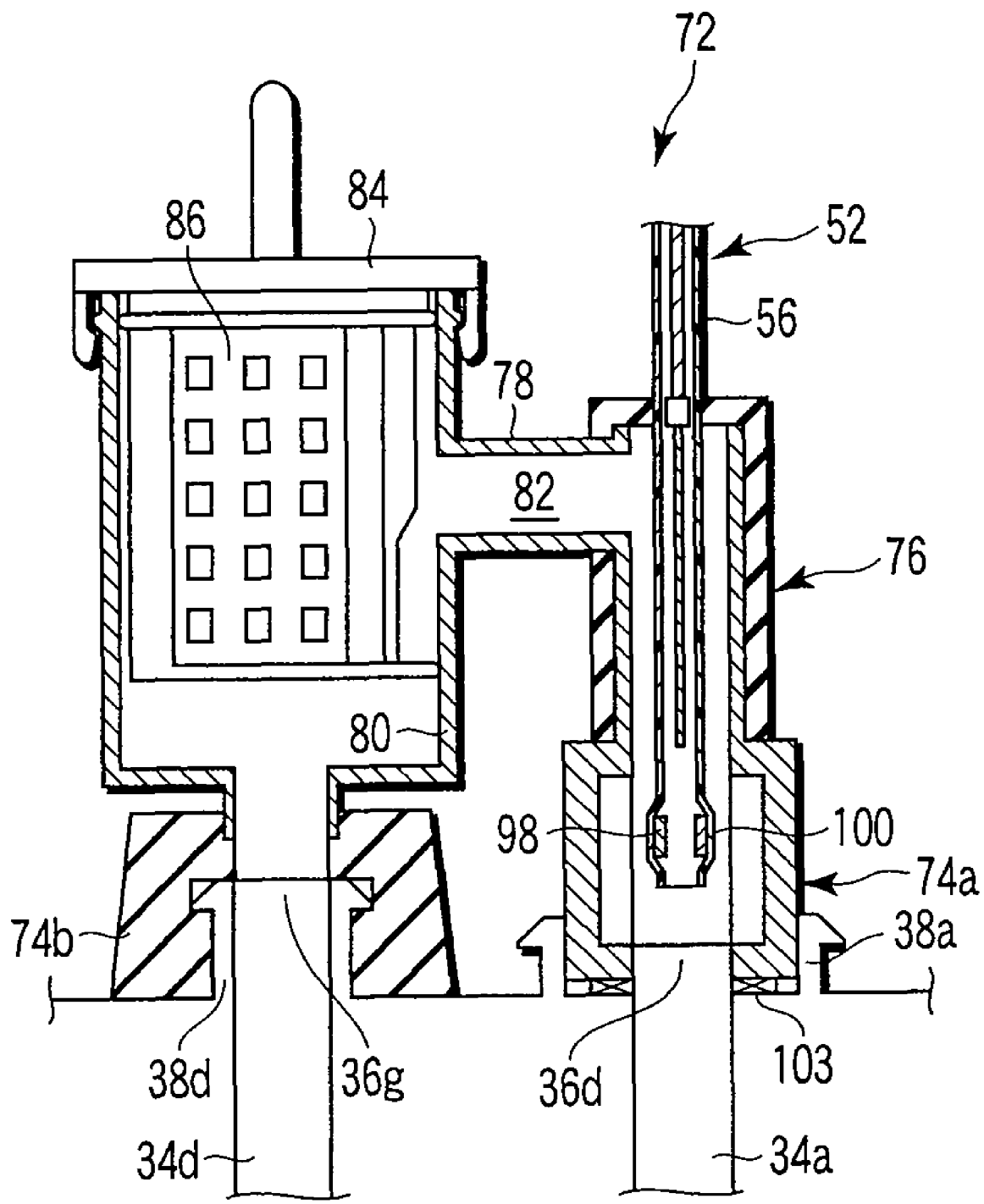
FIG. 14 is a longitudinal cross sectional view viewed in an arrow XIV direction of FIG. 13, showing a state wherein a trap portion of the high-frequency snare is attached to the connecter of the endoscope in the endoscope system according to the second embodiment of the present invention.

Next, an operation of the endoscope system according to the present embodiment will be described with reference to FIGS. 12 to 14. The trap portion 72 is previously arranged at the distal end of the snare portion 52, the plug member 40 is detached from the endoscope 24, and the trap portion 72 is attached to the endoscope 24. As shown in FIG. 12, before the first connection member 74a is connected to the insertion connecter 38a, the distal end of the sheath 56 of the high-frequency snare 50 is held by the holding member 102, and the sheath 56 is fixed to the trap portion 72. As shown in FIGS. 13 and 14, when the first connection member 74a is connected to the insertion connecter 38a, the press protrusions 96 of the claw portions 94 of the insertion connecter 38a press the back surfaces of the hinge portions 104 of the holding members 102 via the window portions 110 of the first connection member 74a, the pair of arm portions 106a, 106b are opened about each hinge portion 104, and the holding of the sheath 56 by the holding members 102 is released, whereby the sheath 56 become movable forward and backward with respect to the trap portion 72. In this state, the distal end surface of the sheath 56 is arranged so as to face the insertion port 36d of the endoscope 24 and, through pushing the sheath 56 inwards, the sheath 56 is inserted into the insertion port 36d directly and through a channel 34a.

Therefore, the endoscope system of the present embodiment has the following effect. In the present embodiment, through arranging the trap portion 72 of the high-frequency snare 50 at the distal end of the sheath 56 and attaching the trap portion 72 to the endoscope 24, the distal end surface of the sheath 56 of the high-frequency snare 50 is arranged so as to face the insertion port 36d of the endoscope 24. Therefore, when the sheath 56 is moved forward with respect to the trap portion 72, the sheath 56 is inserted directly into the insertion port 36d and through the channel 34a. In this manner, an inserting operation of the sheath 56 into the channel 34a is facilitated.

FIGS. 15 to 22B show a third embodiment of the present invention. A configuration having a function similar to that of the second embodiment is denoted with the same reference numerals, and description thereof is omitted. In the endoscope of the present embodiment, a channel for insertion of the sheath of the high-frequency snare is formed separately from a channel for the suction of a polyp or the like.

Figure 15:
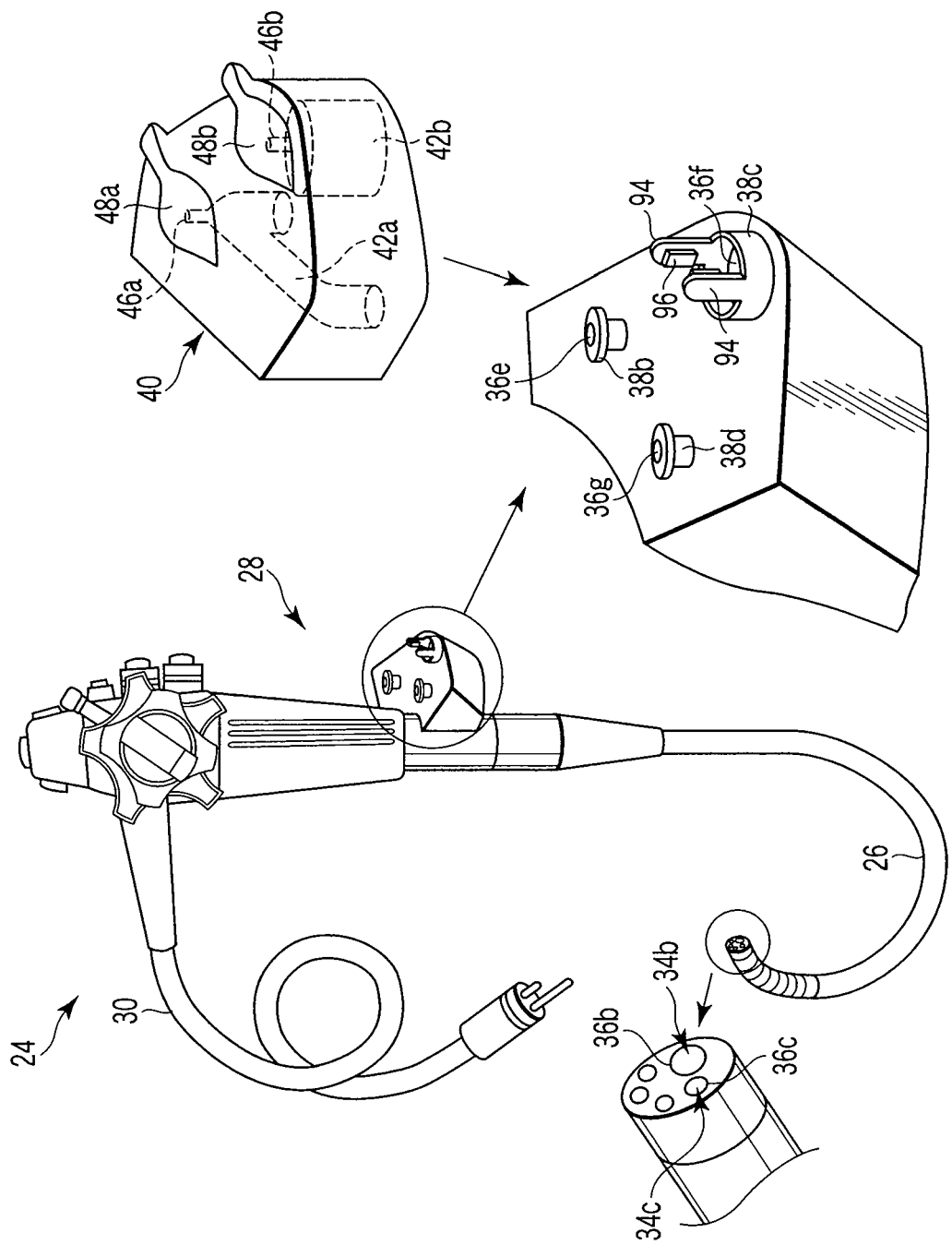
FIG. 15 is a perspective view showing an endoscope and a plug member of an endoscope system according to a third embodiment of the present invention.

FIG. 15 shows the endoscope 24 of the endoscope system according to the present embodiment. The endoscope 24 of the present embodiment is provided with a first channel 34b having a configuration similar to that of the channel 34a (see FIGS. 9A and 9B) of the second embodiment. Furthermore, the endoscope 24 is provided with a second channel 34c for insertion of the sheath 56 (see FIGS. 16A and 16b) of the high-frequency snare 50 separately from the first channel 34b. In the same manner as in the first channel 34b, a distal end of the second channel 34c forms a second distal opening 36c, and a proximal end of the second channel 34c forms a second insertion port 36f as a proximal opening in a second insertion connecter 38c of the operating portion 28. Then, the first insertion port 36e of the first channel 34b, the suction opening 36g and the second insertion port 36f are arranged so as to form a vertex of a triangle.

The plug member 40 is detachably attached to a first insertion connecter 38b of the first channel 34b, the suction connecter 38d and the second insertion connecter 38c. This plug member 40 is provided with a first communication path 42a to communicate the first insertion port 36e with suction opening 36g and having a configuration similar to that of the communication path 42 (see FIGS. 9A and 9B) of the second embodiment. The plug member 40 is provided with a second communication path 42b extending so as to lengthen the second channel 34c in a state wherein the plug member 40 is attached to the second insertion connecter 38c. This second communication path 42b includes a second channel opening 46b and a second lid member 48b having configurations similar to those of a first channel opening 46a of the first communication path 42a and a first lid member 48a.

Moreover, a protruding end surface of the second insertion connecter 38c is provided with a pair of protruding claw portions 94 including press protrusions 96 to cooperate with a holding member 102 (see FIGS. 18A and 18B) described later, respectively.

Figure 16A:
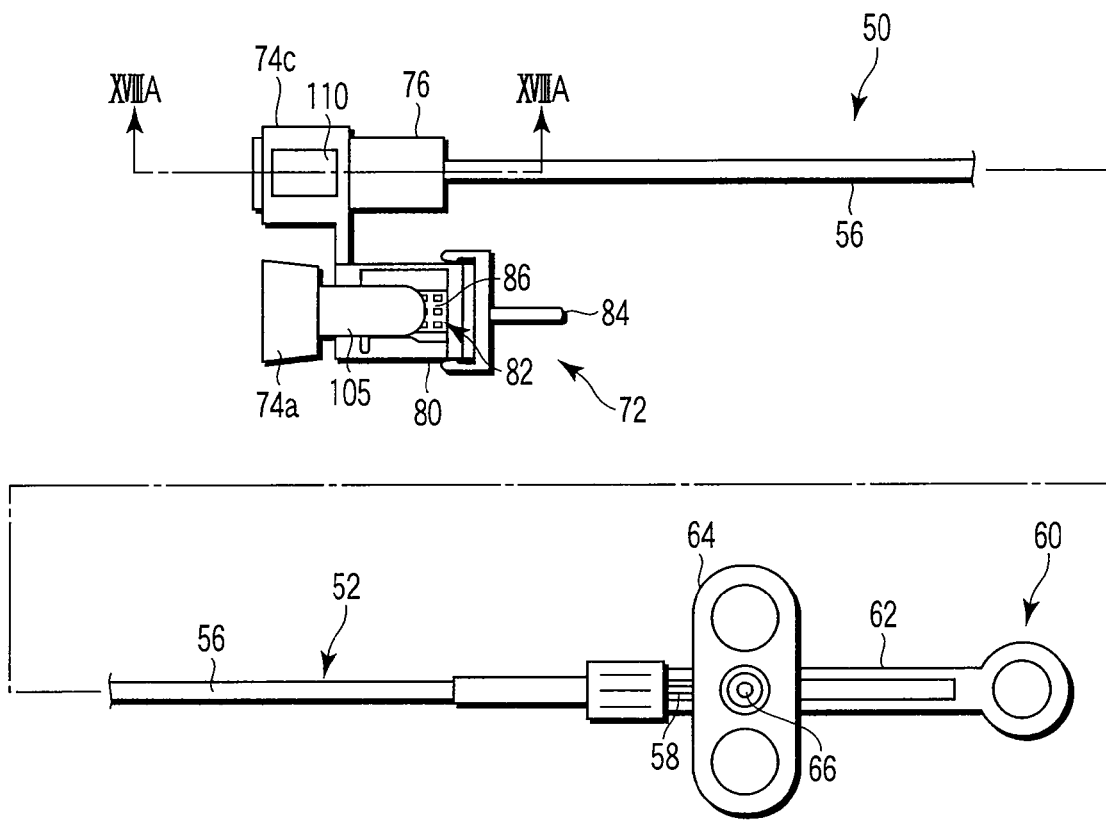
FIG. 16A is a side view showing the high-frequency snare of the endoscope system according to the third embodiment of the present invention.
Figure 16B:
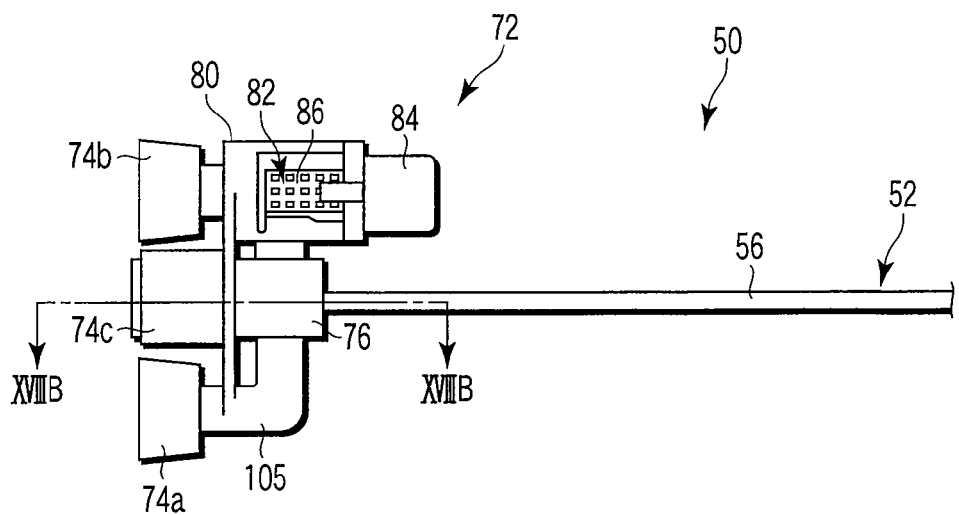
FIG. 16B is a top view showing a distal end of the high-frequency snare of the endoscope system according to the third embodiment of the present invention.

FIGS. 16A to 18C show the high-frequency snare 50 of the endoscope system according to the present embodiment. As shown in FIGS. 16A to 17, in the trap portion 72 of the high-frequency snare 50 according to the present embodiment, inner cavities of the first connection member 74a, an L-shaped tube 105, the case 80 and the second connection member 74b form the communication path 82. Referring to FIGS. 15 to 17, unlike the second embodiment, the first connection member 74a is formed of an elastic material, and connected to the first insertion connecter 38b of the endoscope 24 airtightly to communicate the first insertion port 36e with the communication path 82. The first connection member 74a is connected to the case 80 via the L-shaped tube 105, and the case 80 is connected to the second connection member 74b.

Figure 18B:
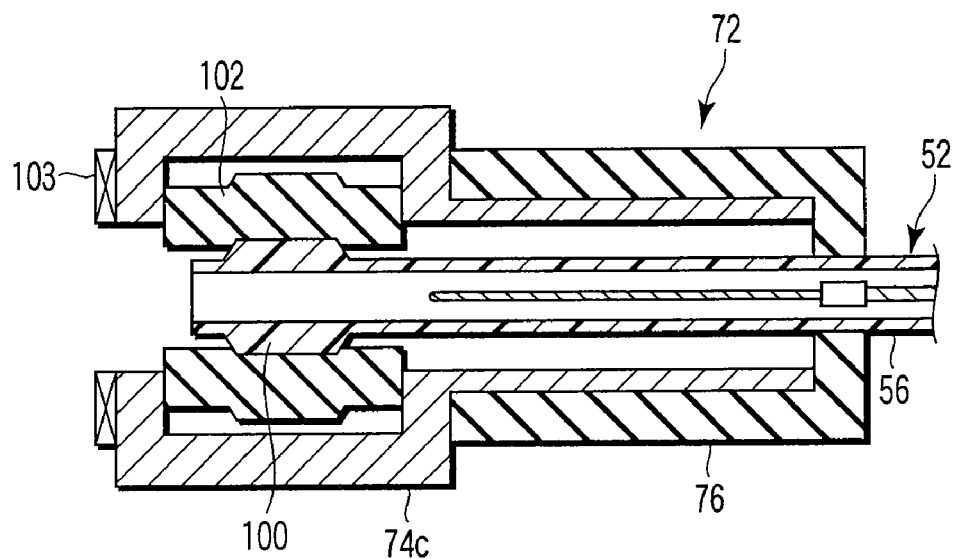
FIG. 18B is a longitudinal cross sectional view along the XVIIIB-XVIIIB line of FIG. 16B, showing the third connection member of the high-frequency snare of the endoscope system according to the third embodiment of the present invention.
Figure 18C:
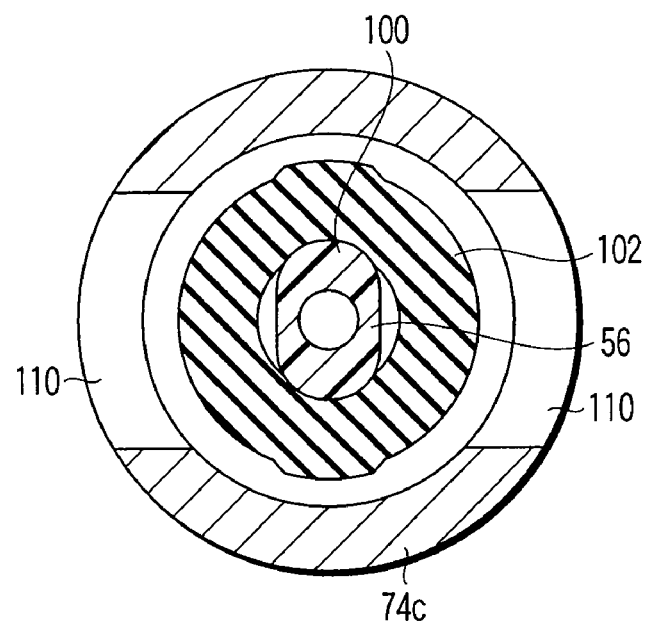
FIG. 18C is a transverse cross sectional view showing the third connection member and its periphery of the high-frequency snare of the endoscope system according to the third embodiment of the present invention.

As shown in FIGS. 18A to 18C, in the trap portion 72, a third connection member 74c to be connected to the second insertion connecter 38c is connected to one end of the insertion tube 76, and the sheath 56 of the snare portion 52 is extractably inserted into the insertion tube 76 and the third connection member 74c.

That is, the third connection member 74c connected to one end of the insertion tube 76 has a substantially cylindrical shape, and the substantially cylindrical holding member 102 is disposed coaxially in this third connection member 74c. It is to be noted that a clearance is formed between an inner peripheral surface of the third connection member 74c and an outer peripheral surface of the holding member 102 so as to allow elastic deformation of the holding member 102 described later. Here, an outer periphery of a cross section of a distal end of the sheath 56 of the snare portion 52 of the high-frequency snare 50, orthogonal to a longitudinal axial direction thereof, has a substantially elliptic shape, and the distal end of the sheath 56 is provided with a pair of protruding portions 100 protruding in mutually opposite directions in one axial direction orthogonal to the longitudinal axis thereof. Then, the distal end of the sheath 56 is inserted into the holding member 102, and an inside diameter of the holding member 102 is larger than a minor axis of the elliptic shape of the distal end of the sheath 56, and shorter than a major axis.

Therefore, the protruding portions 100 of the sheath 56 press an inner peripheral surface of the holding member 102 to elastically deform the holding member 102, and engage with the inner peripheral surface of the holding member 102.

On the other hand, as shown in FIGS. 15 and 18A to 18C, the pair of window portions 110 is formed through the third connection member 74c so as to face each other with a central axis of the third connection member 74c between them. Then, in the same manner as in the second embodiment, when the trap portion 72 is attached to the endoscope 24, the press protrusions 96 of the claw portions 94 of the second insertion connecter 38c press the outer peripheral surface of the holding member 102 via the window portions 110. The pressed holding member 102 is compressed and deformed in a pressed direction, and outer and inner peripheries of a cross section orthogonal to a central axial direction thereof become a substantially elliptic shape wherein the pressed direction is a minor axial direction. Here, the distal end of the sheath 56 is arranged so that the minor axial direction of the elliptic shape of the outer periphery of the cross section substantially matches with the pressed direction. Then, the major and minor axes of the elliptic shape of the inner periphery of the cross section of the deformed holding member 102 become longer than those of the elliptic shape of the outer periphery of the cross section of the sheath 56, respectively (see FIG. 22C), and the engagement between the holding member 102 and the protruding portions 100 of the sheath 56 is released, so that the sheath 56 become movable forward and backward with respect to the third connection member 74c.

Figure 19:
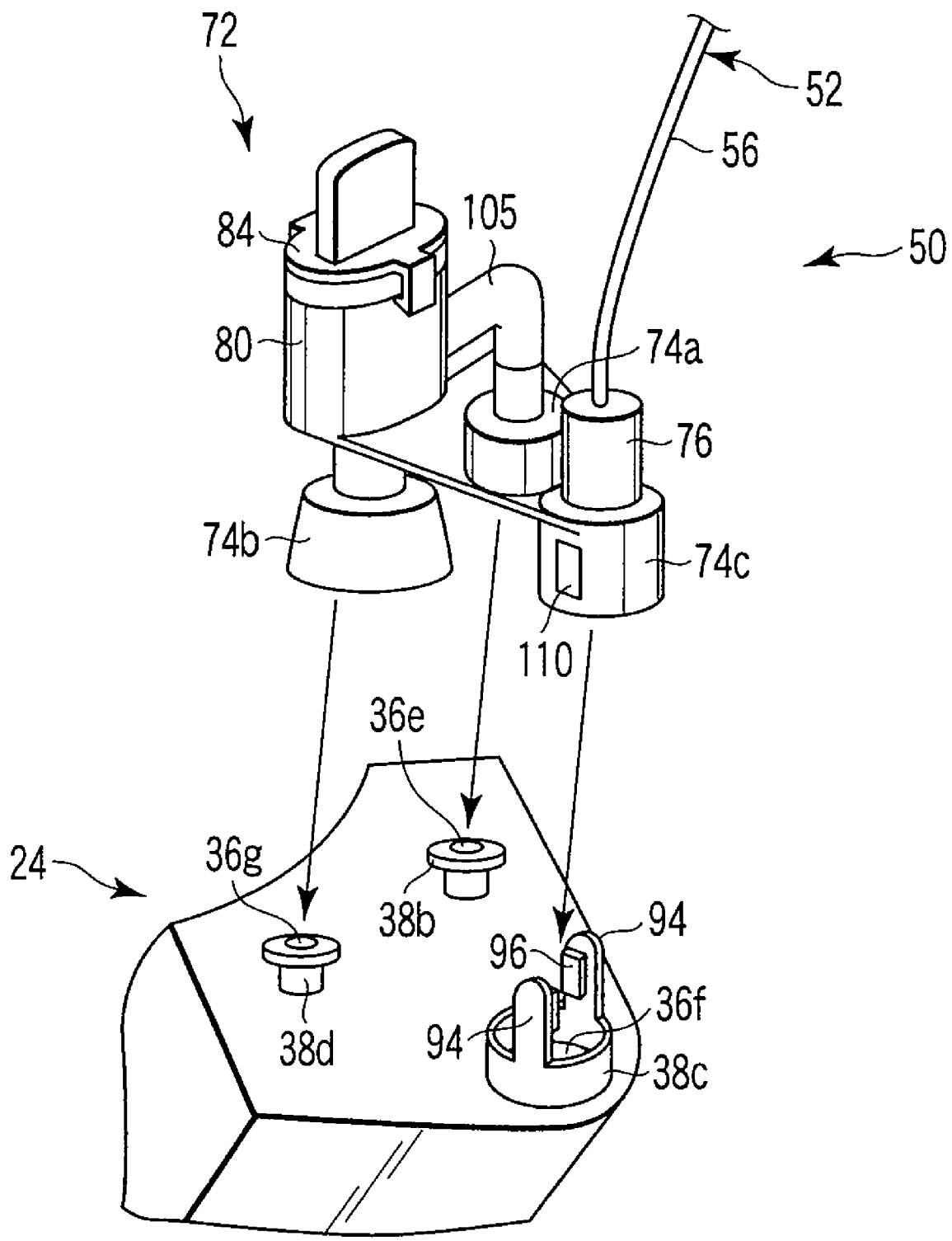
FIG. 19 is a perspective view showing a state before a trap portion of the high-frequency snare is attached to the connecter of the endoscope in the endoscope system according to the third embodiment of the present invention.

Next, an operation of the endoscope system according to the present embodiment will be described with reference to FIGS. 19 to 22C. As shown in FIG. 19, the plug member 40 is detached from the endoscope 24, and the trap portion 72 of the high-frequency snare 50 is attached to the endoscope 24. In this case, the first connection member 74a is connected to the first insertion connecter 38b, the second connection member 74b is connected to the suction connecter 38d, and the third connection member 74c is connected to the second insertion connecter 38c.

Figure 20:
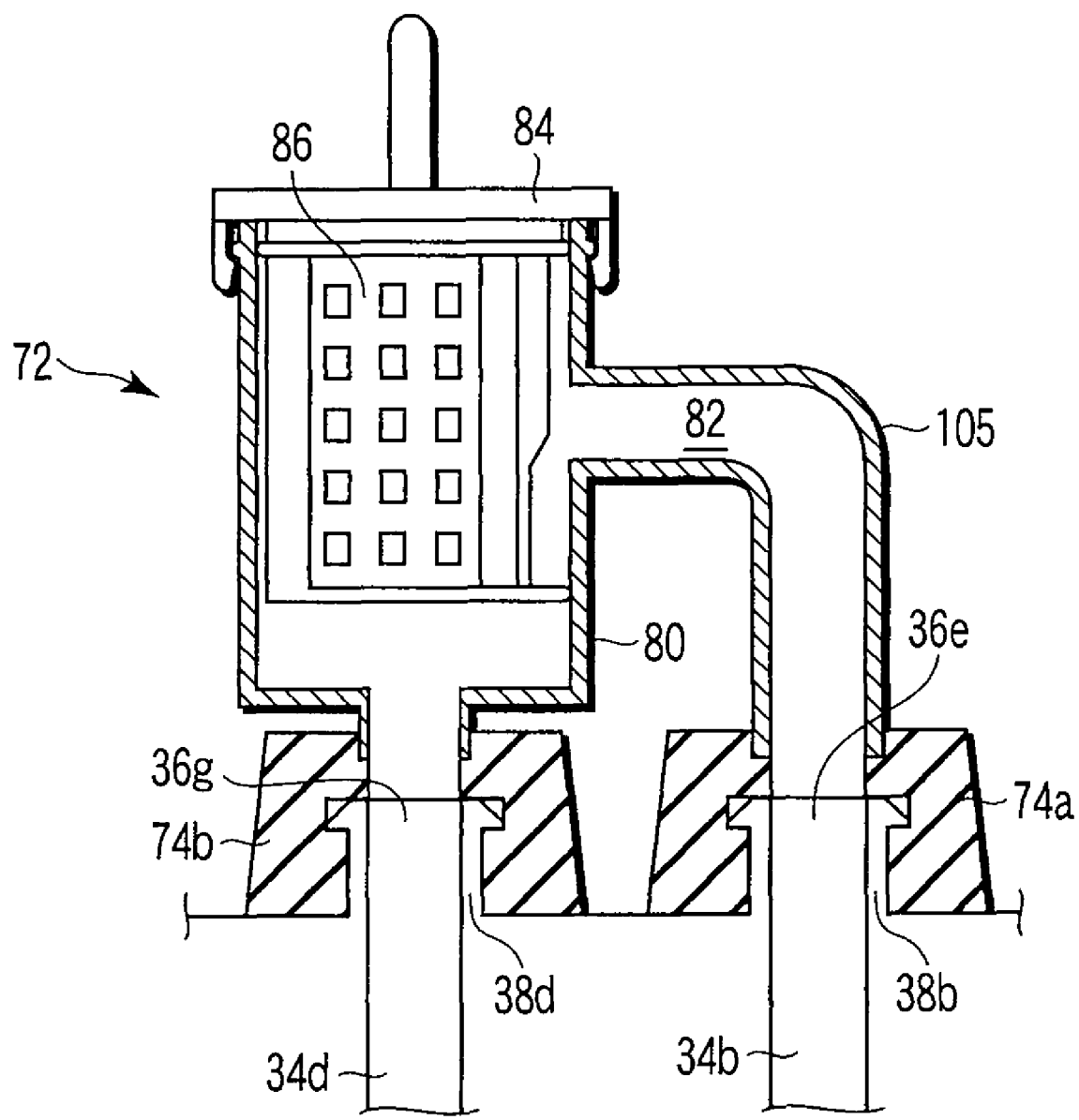
FIG. 20 is a longitudinal cross sectional view showing a state wherein the trap portion of the high-frequency snare is attached to the connecter of the endoscope in the endoscope system according to the third embodiment of the present invention.

As a result, as shown in FIG. 20, the first channel 34b is connected to the suction duct 34d via the communication path 82 of the trap portion 72.

Figure 21:
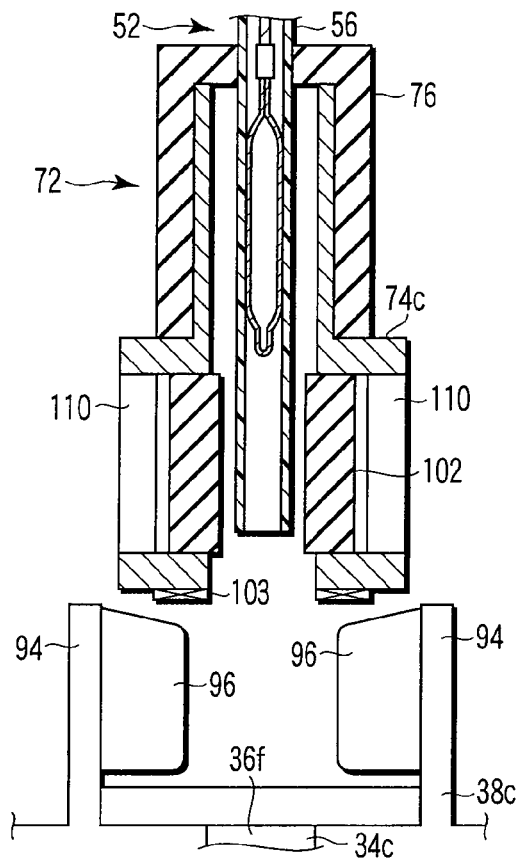
FIG. 21 is a longitudinal cross sectional view showing a state before the third connection member of the high-frequency snare is attached to the second insertion connecter of the endoscope in the endoscope system according to the third embodiment of the present invention.
Figure 22A:
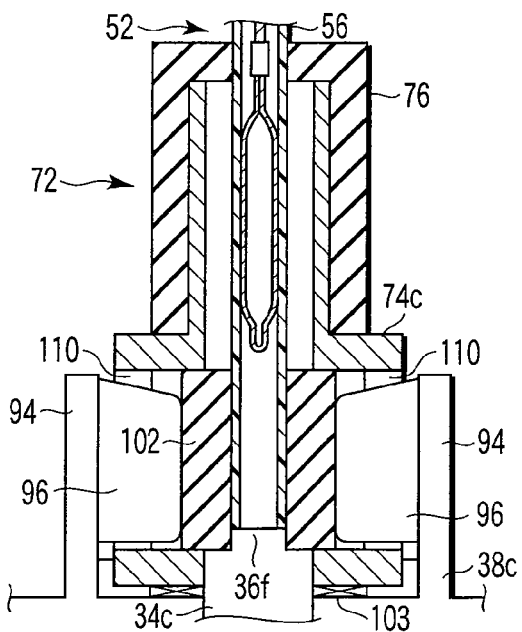
FIG. 22A is a longitudinal cross sectional view showing a state wherein the third connection member of the high-frequency snare is attached to the second insertion connecter of the endoscope in the endoscope system according to the third embodiment of the present invention.
Figure 22B:
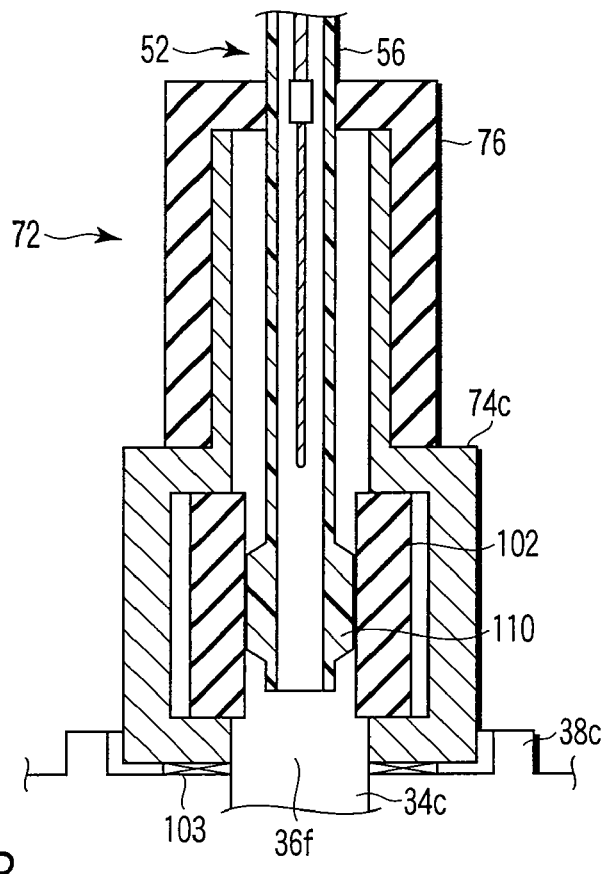
FIG. 22B is another longitudinal cross sectional view showing a state wherein the third connection member of the high-frequency snare is attached to the second insertion connecter of the endoscope in the endoscope system according to the third embodiment of the present invention.
Figure 22C:
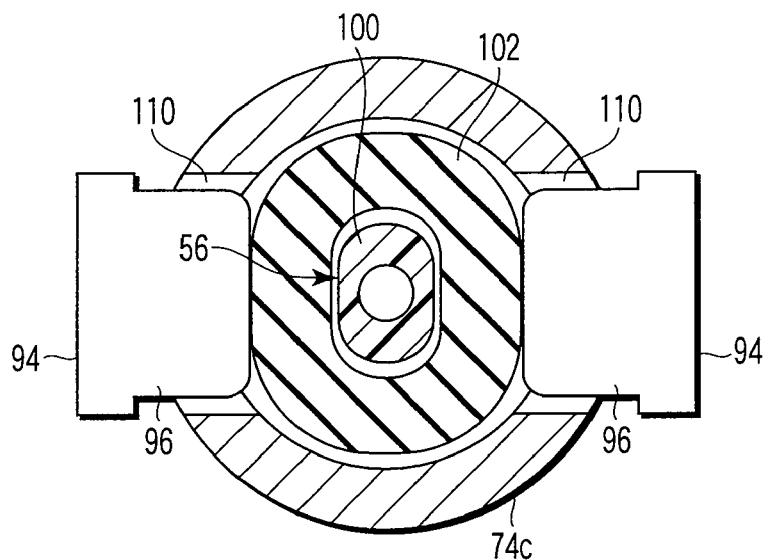
FIG. 22C is a transverse cross sectional view showing a state wherein the third connection member of the high-frequency snare is attached to the second insertion connecter of the endoscope in the endoscope system according to the third embodiment of the present invention.

Moreover, referring to FIG. 21, before the third connection member 74c is connected to the second insertion connecter 38c, the protruding portions 100 of the sheath 56 of the high-frequency snare 50 press the inner peripheral surface of the holding member 102 to elastically deform the holding member 102, and engage with the holding member 102, whereby the sheath 56 is fixed to the trap portion 72. Then, when the third connection member 74c is connected to the second insertion connecter 38c, as shown in FIGS. 22A to 22C, the press protrusions 96 of the claw portions 94 of the second insertion connecter 38c press the outer peripheral surface of the holding member 102 via the window portions 110 of the second connection member 74b. The pressed holding member 102 is elastically deformed into the elliptic cross sectional shape, the major and minor axes of the elliptic shape of the inner periphery of the cross section are larger than those of the elliptic shape of the outer periphery of the cross section of the sheath 56, respectively, the engagement between the holding member 102 and the protruding portions 100 of the sheath 56 is released, and the sheath 56 become movable forward and backward with respect to the trap portion 72.

Afterwards, the sheath 56 is pushed inwards, the sheath 56 is inserted through the second channel 34c from the second insertion port 36f, and the distal end of the sheath is protruded from the second distal opening 36c at the distal end of the endoscope 24 to perform a cutting operation of a polyp 92. When the cut polyp 92 is sucked and gathered, the sheath 56 is not extracted from the second channel 34c, and the polyp 92 is sucked from a first distal opening 36b into the first channel 34b and then the communication path 82, and captured by the mesh portion 86. Subsequently, the cutting, and the sucking and gathering of the polyp 92 are successively repeated.

Therefore, the endoscope system of the present embodiment produces the following effect. In the endoscope 24 of the present embodiment, the second channel 34c for the insertion of the sheath 56 of the high-frequency snare 50 is formed separately from and independently of the first channel 34b for the sucking and gathering of the cut polyp 92. Therefore, when the polyp 92 is sucked and gathered, the snare does not have to be extracted from the endoscope 24, and the cutting, and the sucking and gathering of the polyp 92 can easily be repeated.

In the above embodiments, the endoscope system to cut, and suck and gather the polyp 92 has been described as an example, but the present invention is applicable to any endoscope system to separate a part of a living tissue therefrom in a body cavity under observation with the endoscope and suck and gather the separated tissue.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope system comprising: an endoscope; and an endoscopic accessory, the endoscope including: an elongated insertion portion insertable from a distal end thereof into a body cavity; an operating portion connected to a proximal end of the insertion portion; a channel provided at the insertion portion and the operating portion, of which a distal end forms a distal opening at the distal end of the insertion portion, of which a proximal end forms a proximal opening at the operating portion, and used for at least suction; and a suction duct provided at the operating portion, of which a distal end forms a suction opening at the operating portion, and of which a proximal end is connected to a suction device, and the endoscopic accessory including: an elongated accessory insertion portion insertable from a distal end thereof into the body cavity; a treatment portion provided at the distal end of the accessory insertion portion and to separate a part of a living tissue therefrom; and a capture portion to be connected to the accessory insertion portion and detachably attached to the operating portion of the endoscope, and the capture portion including: a communication path to communicate the proximal opening with the suction opening when the capture portion is attached to the endoscope; and a capture unit interposed in the communication path and to capture the tissue being sucked from the channel into the suction duct.

2. The endoscope system according to claim 1,
wherein the capture portion is connected to the accessory insertion portion so that the accessory insertion portion is movable forward and backward in a longitudinal axial direction of the accessory insertion portion with respect to the capture portion.

3. The endoscope system according to claim 2, further comprising
a switch mechanism to switch the endoscopic accessory between a fixed state wherein the accessory insertion portion is fixed to the capture portion and a released state wherein the fixing is released.

4. The endoscope system according to claim 3,
wherein the switch mechanism brings the endoscopic accessory into the fixed state when the capture portion is detached from the endoscope and brings the endoscopic accessory into the released state when the capture portion is attached to the endoscope.

5. The endoscope system according to claim 2,
wherein the channel is configured so that the accessory insertion portion is insertable through the channel from the proximal opening, and
the capture portion is configured to be arranged at the distal end of the accessory insertion portion, and a distal end surface of the accessory insertion portion is arranged so as to face the proximal opening when the capture portion is arranged at the distal end of the accessory insertion portion and attached to the endoscope.

6. The endoscope system according to claim 1,
wherein the endoscope further includes another channel provided at the insertion portion and the operating portion, of which a distal end forms another distal opening at the distal end of the insertion portion, of which a proximal end forms another proximal opening at the operating portion and through which the accessory insertion portion is insertable from the other proximal opening.

7. An endoscopic accessory of an endoscope system, the endoscope system comprising: an endoscope; and the endoscopic accessory,
the endoscope including: an elongated insertion portion insertable from a distal end thereof into a body cavity; an operating portion connected to a proximal end of the insertion portion; a channel provided at the insertion portion and the operating portion, of which a distal end forms a distal opening at the distal end of the insertion portion, of which a proximal end forms a proximal opening at the operating portion, and used for at least suction; and a suction duct provided at the operating portion, of which a distal end forms a suction opening at the operating portion, and of which a proximal end is connected to a suction device, and
the endoscopic accessory including: an elongated accessory insertion portion insertable from a distal end thereof into the body cavity; a treatment portion provided at the distal end of the accessory insertion portion and to separate a part of a living tissue therefrom; and a capture portion to be connected to the accessory insertion portion and detachably attached to the operating portion of the endoscope, and the capture portion including: a communication path to communicate the proximal opening with the suction opening when the capture portion is attached to the endoscope; and a capture unit interposed in the communication path and to capture the tissue being sucked from the channel into the suction duct.

8. An endoscope of an endoscope system,
the endoscope system comprising: an endoscope; and the endoscopic accessory,
the endoscope including: an elongated insertion portion insertable from a distal end thereof into a body cavity; an operating portion connected to a proximal end of the insertion portion; a channel provided at the insertion portion and the operating portion, of which a distal end forms a distal opening at the distal end of the insertion portion, of which a proximal end forms a proximal opening at the operating portion, and used for at least suction; and a suction duct provided at the operating portion, of which a distal end forms a suction opening at the operating portion, and of which a proximal end is connected to a suction device, and
the endoscopic accessory including: an elongated accessory insertion portion insertable from a distal end thereof into the body cavity; a treatment portion provided at the distal end of the accessory insertion portion and to separate a part of a living tissue therefrom; and a capture portion to be connected to the accessory insertion portion and detachably attached to the operating portion of the endoscope, and the capture portion including: a communication path to communicate the proximal opening with the suction opening when the capture portion is attached to the endoscope; and a capture unit interposed in the communication path and to capture the tissue being sucked from the channel into the suction duct.

* * * * *